United States Patent [19]

Miyazono et al.

[11] Patent Number: 5,278,247
[45] Date of Patent: Jan. 11, 1994

[54] UREA-SUPERACID SALTS AND THEIR USE AS A CURING CATALYST OF EPOXY RESINS

[75] Inventors: Tadafumi Miyazono, Mino; Koji Tabuchi, Takatsuki, both of Japan

[73] Assignee: Nippon Paint Co., Ltd., Osaka, Japan

[21] Appl. No.: 872,699

[22] Filed: Apr. 24, 1992

[30] Foreign Application Priority Data

Apr. 25, 1991 [JP] Japan .................... 3-125055

[51] Int. Cl.$^5$ .................................. C08G 59/68
[52] U.S. Cl. .................. 525/327.3; 528/88; 528/89; 528/90; 528/91; 528/92; 528/93; 528/94; 528/361; 528/393; 528/408; 528/409; 528/410
[58] Field of Search .......... 528/88, 89, 90, 91, 528/92, 93, 94, 361, 393, 408, 409, 410; 525/327.3

[56] References Cited

U.S. PATENT DOCUMENTS

| | | | |
|---|---|---|---|
| 3,711,390 | 1/1973 | Feinberg | 528/91 |
| 3,842,019 | 11/1974 | Kropp | 528/90 |
| 4,101,459 | 7/1978 | Andrews | 528/118 |
| 4,360,649 | 11/1982 | Kamio et al. | 525/484 |
| 4,503,211 | 3/1985 | Robins | 528/92 |
| 4,650,834 | 3/1987 | Yagishita et al. | 525/327.3 |
| 4,668,758 | 5/1987 | Corley | 528/91 |
| 4,931,509 | 6/1990 | Yagishita et al. | 525/327.3 |
| 5,039,756 | 8/1991 | Yamamoto et al. | 525/327.3 |
| 5,082,903 | 1/1992 | Yokoi | 525/327.3 |

FOREIGN PATENT DOCUMENTS 0177044 10/1982 Japan .

*Primary Examiner*—Frederick Krass
*Attorney, Agent, or Firm*—Millen, White, Zelano, & Branigan

[57] ABSTRACT

As a curing catalyst of epoxy resins, superacid salts of an N,N'-di- or N,N',N'-trisubstituted urea, the urea component of which is produced by reacting an organic isocyanate and a primary or secondary amine, at least one of which is monofunctional, are soluble in conventional organic solvents, compatible with epoxy resins and catalyze the cationic polymerization reaction of epoxy resins at room temperature.

16 Claims, No Drawings

UREA-SUPERACID SALTS AND THEIR USE AS A CURING CATALYST OF EPOXY RESINS

BACKGROUND OF THE INVENTION

Epoxy resins are known to have excellent heat-resistant, adhesive, antichemical, electrical, mechanical and other properties and, therefore, have extensively been used in various fields as adhesives, coatings, sealants, insulating materials, casting and molding materials and the like.

Two systems are employed to harden or cure the epoxy resin; one using a polyamine or polycarboxylic acid or anhydride hardener and the other being a self-polymerization system containing a cationic or anionic polymerization initiator generally referred to as "curing catalyst".

A variety of curing catalyst are known including Bronsted acids, Lewis acid, tertiary amine-superacid salts and the like. These known curing catalysts have certain defects in that they are solid or not soluble in conventional solvents such as toluene or are xylene or not fully compatible with the epoxy resin so that they can be uniformly dispersed in the epoxy resin only with difficulty. This can result in incomplete or localized curing of the resin. Furthermore, the prior art curing catalysts are generally capable of curing of alicyclic epoxy compounds or resins at room temperature but not non-alicyclic epoxy compounds or resins which are less reactive than the alicyclic epoxy resins.

A need exists, therefore, for a curing catalyst of epoxy resins which is soluble in conventional organic solvents such as toluene and xylene, highly compatible with epoxy resins and capable of curing non-alicyclic epoxy compounds or resins at room temperature. Also, a need exists for a resinous composition containing a polyfuctional epoxy compound or resin and such a hardening catalyst.

SUMMARY OF THE INVENTION

In accordance with the present invention, the above and other needs are met by a curing catalyst for epoxy resins consisting essentially of a superacid salt of an N,N'-di- or N,N,N'-trisubstituted urea produced by reacting an isocyanate and a primary or secondary amine, at least one of said isocyanate and said amine being monofunctional.

The present invention also provides a resinous composition comprising an organic epoxy compound or resin having a plurality of epoxide groups in the molecule and a catalytically effective amount of said urea-superacid salt.

DETAILED DESCRIPTION

N,N'-di- or N,N,N'-trisubstituted Ureas

The reaction of an isocyanate and a primary or secondary amine is well-known in organic chemistry as a synthesis of di- or trisubstituted ureas. The substituted ureas used in the present invention may easily synthesized using this well-known method. A typical example of the synthesis includes the reaction of a primary or secondary monoamine and a monoisocyanate to produce the corresponding N,N'-di- or N,N,N'-trisubstituted urea. The present invention includes not only the superacid salt of such monourea but also the salt with a polyurea produced by reacting a polyamine with a monoisocyanate and vice versa. In other words, at least one of the amine and isocyanate reactants must be monofunctional. The reaction of a polyisocyanate and a polyamine results in, as is well-known, a polyurea elastomer polymer and is, therefore, excluded from the urea component of the present invention.

Examples of primary and secondary monoamines usable in the synthesis of the above substituted ureas include methylamine, dimethylamine, ethylamine, diethylamine, propylamine, dipropylamine, butylamine, dibutylamine, amylamine, diamylamine, hexylamine, dihexylamine, 2-ethylhexylamine, di-2-ethylhexylamine, octylamine, dioctylamine, laurylamine, dilaurylamine, stearylamine, disteraylamine, benzylamine, allylamine, aniline, o-, m- and p-toluidine, naphthylamine, mono- and diethanolamine and the like. Hybrid secondary monoamines of the above-named primary amines such as benzylmethylamine may also be used.

Examples of monoisocyanates include those derived from the above-named primary monoamines by reacting with phosgene. The reaction between the monoamine and the monoisocyanate gives the corresponding N,N'-di- or N,N,N'-trisubstituted urea. In contrast with this, when one of the amine and isocyanate reactants is polyfunctional, a compound having a plurality of urea linkage will result.

A variety of polyfunctional isocyanates are known in polyurethane and polyurea chemistry and include hexamethylenediisocyanate, tolylenediisocyanate, 4,4'-diphenylmethanediisocyanate, xylylenediisocyanate, lysin diisocyanate, 4,4'-methylenebis(cyclohexylisocyanate), methylcyclohexane-2,4-(or 2,6-) diisocyanate, 1,3-bis (isocyanatomethyl)-cyclohexane, isophoronediisocyanate, trimethylhexamethylenediisocyanate, dimer acid diisocyanate, trimers of hexamethylenediisocyanate (biuret or isocyanurate) and the like.

Examples of polyfunctional primary and secondary amines usable for the same purpose include ethylenediamine, trimethylenediamine, tetramethylenediamine, pentamethylenediamine, hexamethylenediamine and the like. Also included in this class are polyfunctional primary amines corresponding to the above-exemplified organic polyisocyanates. In other words, the very same substituted urea compounds will result starting from a polyfunctional primary amine and a monofunctional primary amine by reacting either one of amines with phosgene and then with the remaining amine.

Superacid Salts of Substituted Ureas

The term "superacid" as used herein is defined as an acid having an acidity stronger than a 100% sulfuric acid. See Kirk-Othmer, *Enc. of Chem. Tech.* (3rd Ed.), Vol. 11, pp. 295-296. Urea and substituted ureas exhibit a weak basicity and may bind a superacid in the form of a quarternary ammonium salt.

Such salts may be produced by reacting the urea component with an alkali metal salt of a superacid under acidic conditions with hydrochloric acid. The reaction may be carried out, for example, by dissolving the urea component in an suitable organic solvent, acidified with hydrogen chloride on hydrochloric acid and then adding a solution of an alkali metal salt of a superacid. After removing precipitated alkali metal chloride by-product, desired urea-superacid salt may be recovered by evaporation. The product may be further purified by extraction, recrystallization or other conventional methods.

Examples of alkali metal salts of superacids include $NaSbF_6$, $NaBF_4$, $NaAsF_6$, $NaPH_6$, $NaCF_3SO_3$, $KSbF_6$, $KBF_4$, $KAsF_6$, $KPF_6$, $KCF_3SO_3$ and the like.

The resulting superacid salts are soluble in conventional organic solvents including aromatic hydrocarbons such as toluene and xylene, esters such as butyl acetate and ethyl acetate. They are compatible with a variety of epoxy resins and may initiate their cationic polymerization by releasing a proton at room or elevated temperatures. Their activity as a cationic polymerization initiator may vary with the hydrocarbon substituent of urea component and also with particular superacids. However, the activity of urea salts of the above-named superacids are strong enough to initiate the cationic polymerization of non-alicyclic epoxy resins even at room temperature. This has been very difficult with prior art curing catalysts.

Curable Resin Compositions

The curing catalyst of the present invention may be used in conjunction with a compound or resin having a plurality of epoxy groups. The epoxy group may be alicyclic or non-alicyclic such as glycidyl.

Specific examples of alicyclic polyepoxy compounds include 3,4-epoxycyclohexyloxirane, 3',4'-epoxycyclohexylmethyl-3,4-epoxycyclohexylcarboxylate, 1,2,5,6-diepoxyperhydroindene, 2-(3,4-epoxycyclohexyl)-3',4'-epoxy-1,3-dioxane-5-spirocyclohexane, 1,2-ethylenedioxy-bis(3,4-epoxycylohexylmethane), 1,3-dimethyl-2,3-epoxycyclohexyloxirane, di-(2,3-epoxycyclopentyl)ether, 4',5'-epoxy-2'-methylcyclohexylmethyl-4,5-epoxy-2-methylcyclohexanecarboxylate, 3',4'-epoxy-2'-methylcyclohexylmethyl-3,4-epoxy-2-methylcyclohexanecarboxylate, bis(3,4-epoxycyclohexylmethyl)adipate, bis(4,5-epoxy-2-methylcyclohexylmethyl)adipate, ethylene glycol-bis(3,4-epoxycyclohexanecarboxylate) and the like.

Examples of polyfunctional non-alicyclic epoxy resins include polyglycidyl ethers of polyhydric phenols such as bisphenol A, tetrabromobisphenol A, bisphenol S, phenol novolac or cresol novolac; polyglycidyl ethers of polyhydric alcohols such as butanediol, hexanediol, hydrogenated bisphenol A or dimethylolbenzene; polyglycidyl esters of polycarboxylic acids such as terephthalic, isophthalic, phthalic or adipic acid; and glycidyl esterether of hydroxycarboxylic acid such as p-hydroxybenzoic acid.

A further class of epoxy resins include homo- or copolymers of such epoxy group-containing acrylic monomers. Typical examples of acrylic monomers having a nonalicyclic group are glycidyl acrylate and glycidyl methacrylate. Examples of acrylic monomers having an alicyclic epoxy group include 3,4-epoxycyclohexylmethyl (meth)acrylate, (meth)acrylate of the adduct of poly-ε-caprolactone with 3,4-epoxycylohexylmethanol and reaction products of (meth)acrylic acid and the above-named polyfunctional alicyclic epoxy compounds. Examples of monomers copolymerizable with the epoxy group-containing acrylic monomers include methyl (meth)acrylate, n-butyl (meth)acrylate, isobutyl (meth)acrylate, 2-ethylhexyl (meth)acrylate, 2-hydroxyethyl(meth)acrylate, polycaprolactone glycol mono(meth)acrylate, styrene, acrylonitrile, vinyl acetate and the like.

The above polyfunctional epoxy compounds and polyfunctional epoxy group-containing resins may be used singly or in combination.

The composition of the present invention may contain as a chain-extender on cross-linker a minor amount of a polyhydric alcohol such as ethylene glycol, propylene glycol, 1,4-butanediol, 1,3-butanediol, 2,3-butanediol, diethylene glycol, dipropylene glycol, triethylene glycol, 1,5-pentanediol, 1,6-hexanediol, neopentyl glycol, 2,2,4-trimethylpentane-1,3-diol, glycerine, trimethylolpropane, trimethylene glycol, polyethylene glycol, polycaprolactone glycol, pentaerythritol, dipentaerythritol and the like. Also included are acryl polyols produced by polymerizing hydroxy group-containing acrylic monomers such as 2-hydroxyethyl (meth)acrylate.

The curing catalyst of the present invention may generally be added in an amount of 0.1 to 10% by weight based on the total nonvolatile content of the film-forming components. The exact amount will vary depending upon the type of epoxy resins, properties desired in the cured products, the length of pot life as desired and other parameters. Within the above range it is possible to cure non-alicyclic epoxy resins at room temperature. If necessary, the composition of the present invention may be cured at an elevated temperature.

The resinous composition may contain a variety of conventional additives depending upon its intended use. For example, when used for coating purposes, the composition may contain pigments, solvents, light stabilizers, surface conditioners and the like. Other uses or applications includes adhesives, sealants or potting compounds, casting compounds and other resinous compositions where room temperature-curing is desired.

The following examples are intended to further illustrate the present invention without limiting thereto. All parts and percents therein are by weight unless otherwise indicated.

EXAMPLE 1

N,N-di-(2-ethylhexyl)-N'-n-butylurea hexafluoroantimonate

A four necked flask equipped with a thermometer, stirrer and drip funnel was charged with 4.82 g of di-(2-ethylhexyl)amine and 100 g of ethyl acetate. To this was added dropwise a solution of 1.98 g of n-butylisocyanate in 30 g of ethyl acetate with stirring over 30 minutes while maintaining the inner temperature at 10° C. and allowed to react until the absorption of isocyanate group at 2240 $cm^{-1}$ disappeared IR spectrometrically. Then a mixture of 2.086 g of 35% hydrochloric acid and 50 g of methanol was added dropwise over 30 minutes and allowed to react at room temperature for 20 hours. To this was added dropwise a solution of 5.18 g of $NaSbF_6$ in 50 g of methanol over 30 minutes and allowed to react at room temperature for 20 hours. Then the reaction mixture was filtered to remove NaCl by-product and evaporated to remove the solvent. 11 g of the title compound was obtained as a pale reddish liquid. This product is hereinafter referred to as "curing catalyst A". This catalyst is soluble in aromatic hydrocarbon solvents such as toluene and xylene as well as esters such as butyl acetate and ethyl acetate.

Assignment of Ir spectra:
$SbF_6^-$: 663.4 $cm^{-1}$
Urea: 3100–3400 $cm^{-1}$, 1600–1700 $cm^{-1}$
Ammonium: about 2500 $cm^{-1}$

EXAMPLE 2

N-n-butyl-N'-octylurea triflate

A four necked flask equipped with a thermometer, stirrer and drip funnel was charged with 2.58 g of octylamine and 200 g of ethyl acetate. To this was added dropwise a solution of 1.98 g of n-butylisocyanate in 30 g of ethyl acetate with stirring over 30 minutes while maintaining the inner temperature at 10° C. and allowed to react until the absorption of isocyanato group (2240 cm$^{-1}$) disappeared IR spectrometrically. After dissolving the solidified reaction product in 50 g of methanol, a mixture of 2.086 g of 35% hydrochlonic acid and 50 g of methanol was added dropwise to the solution over 30 minutes and allowed to react at room temperature for 20 hours. Then a solution of 3.44 g of sodium triflate in 50 g of methanol was added dropwise over 30 minutes and allowed to react at room temperature for 20 hours. The reaction mixture was then filtered to remove NaCl by-product and evaporated to remove methano. 8.9 g of the title compound was obtained as a pale yellow liquid. This product is hereinafter referred to as "curing catalyst B". This product is soluble in aromatic hydrocarbon solvents such as toluene and xylene as well as esters such as butyl acetate and ethyl acetate.

Assignment of IR spectra:
$CF_3SO_3^-$: 638.3 cm$^{-1}$, 1031.7 cm$^{-1}$, 1172.5 cm$^{-1}$
Urea: 3100-3400 cm$^{-1}$, 1600-1700 cm$^{-1}$
Ammonium: about 2500 cm$^{-1}$

EXAMPLE 3

N,N-di-(2-ethylhexyl)-N'-naphthylurea hexafluoroantimonate

Example 1 was repeated except that 3.38 g of naphthylisocyanate was substituted for the 1.98 g of n-butylisocyanate. 11.6 g of the title compound was obtained as a pale brown liquid. This product, hereinafter referred to as "curing catalyst C", is soluble in aromatic hydrocarbon solvents such as toluene and xylene as well as ester solvents such as butyl acetate and ethyl acetate.

Assignment of IR spectra:
$SbF_6^-$: 663.4 cm$^{-1}$
Urea: 3100-3400 cm$^{-1}$, 1600-1700 cm$^{-1}$
Ammonium: about 2500 cm$^{-1}$

EXAMPLE 4

N-n-butyl-N'-octylurea hexafluoroantimonate

Example 2 was repeated except that 5.18 g of sodium hexafluoroantimonate was substituted for the 3.44 g of sodium triflate. 9 g of the title compound was obtained as a pale red liquid. This product, hereinafter referred to as "curing catalyst D", is soluble in aromatic hydrocarbon solvents such as toluene xylene as well as esters such as butyl acetate and ethyl acetate.

Assignment of IR spectra:
$SbF_6^-$: 663.4 cm$^{-1}$
Urea: 3100-3400 cm$^{-1}$, 1600-1700 cm$^{-1}$
Ammonium: about 2500 cm$^{-1}$

EXAMPLE 5

N,N-di-(2-ethylhexyl)-N'-n-butylurea triflate

Example 1 was repeated except that 3.44 g of sodium triflate was replaced for 5.18 g of sodium hexafluoroantimonate. 9.2 g of the title compound was obtained as a pale red liquid. This product is soluble in aromatic hydrocarbon solvents such as toluene and xylene as well as esters such as butyl acetate and ethyl acetate, and hereinafter is referred to as "curing catalyst E".

Assignment of IR spectra:
$CF_3SO_3^-$: 638.3 cm$^{-1}$, 1031.7 cm$^{-1}$, 1172.5 cm$^{-1}$
Urea: 3100-3400 cm$^{-1}$, 1600-1700 cm$^{-1}$
Ammonium: about 2500 cm$^{-1}$

EXAMPLE 6

Curing catalyst F

Example 1 was repeated except that 3.86 g of Coronate EH(trifunctional isocyanate produced by Nippon Polyurethane Co., Ltd.) was substituted for the 1.98 g of n-butylisocyanate. 12 g of curing catalyst F was obtained as a pale red liquid. This product is soluble in ester solvents such as butyl acetate and ethyl acetate.

Assignment of IR spectra:
$SbF_6^-$: 663.4 cm$^{-1}$
Urea: 3100-3400 cm$^{-1}$, 1600-1700 cm$^{-1}$
Ammonium: about 2500 cm$^{-1}$

EXAMPLE 7

Curing catalyst G

Example 2 was repeated except that 1.7 g of isophoronediamine was substituted for the 2.58 g of octylamine. 6 g of curing catalyst G was obtained as a pale yellow liquid. This product is soluble in ester solvent such as butyl acetate and ethyl acetate.

Assignment of IR spectra:
$CF_3SO_3^-$: 638.4 cm$^{-1}$, 1031.7 cm$^{-1}$, 1172.5 cm$^{-1}$
Urea: 3100-3400 cm$^{-1}$, 1600-1700 cm$^{-1}$
Ammonium: about 2500 cm$^{-1}$

PRODUCTION EXAMPLE 1

Glycidyl Group-Containing Acrylic Resin

A flask equipped with a thermometer, stirrer and drip funnel was charged with 500 g of xylene and 450 g of butyl acetate and heated to 120° C. To this was added dropwise the following monomeric mixture over 3 hours.

| | |
|---|---|
| Styrene | 400 g |
| Glycidyl methacrylate | 354 g |
| 2-Hydroxyethyl methacrylate | 162 g |
| n-Butyl acrylate | 84 g |
| t-Butylperoxy-2-ethylhexanoate | 37 g |
| Total | 1037 g |

After the addition, the mixture was stirred for additional 30 minutes at 120° C. Then a solution of 5 g of t-butylperoxy-2-ethylhexanoate in 50 g of ethyl acetate was added dropwise. The mixture was stirred for additional 1.5 hours at 120° C. and then cooled down.

A colorless, transparent and viscous resin solution having a nonvolatile content of 50% was obtained. Number mean molecular weight of the resin measured by the GPC method was 5500.

PRODUCTION EXAMPLE 2

Alicylic Epoxy Group-Containing Acrylic Resin

Production Example 1 was repeated except that 3, 4-epoxycyclohexyl methacrylate was substituted for the glycidyl methacrylate.

A colorless, transparent and viscous resin solution having a nonvolatile content of 50% was obtained. Number mean molecular weight of the resin measured by the GPC method was 5200.

EXAMPLES 8–14

Various resin compositions were formulated as indicated in Table 1, applied on a tinplate by a bar coater to a dry film thickness of about 20 μm and allowed to stand at room temperature for 24 hours. The resulting specimens were tested for solvent resistance by rubbing the coated surface with xylene-impregnated fabric at 20 reciprocations and for pencil hardness according to JIS K 5400 6.14. All curing catalyst were used as a 50% solution in butyl acetate. The results are also shown in Table 1.

TABLE 1

| Component, parts | Example 8 | 9 | 10 | 11 | 12 | 13 | 14 |
|---|---|---|---|---|---|---|---|
| Resin of Production Ex. 1 | | | 100 | 100 | | 50 | |
| Resin of Production Ex. 2 | | 100 | | | 100 | | 50 |
| Celloxide 2021[(1)] | | | | | | | 25 |
| Epikote 1001[(2)] | 50 | | | | | 25 | |
| Butyl acetate | 50 | | | | | 25 | 25 |
| Catalyst A | 1.0 | | | | | | |
| Catalyst B | | 1.0 | | | | | |
| Catalyst C | | | 1.0 | | | | |
| Catalyst D | | | | 1.0 | | | |
| Catalyst E | | | | | 1.0 | | |
| Catalyst F | | | | | | 1.0 | |
| Catalyst G | | | | | | | 1.0 |
| Solvent resistance | No Change | No Change | No Change | No Change | No Change | No Change | No Change |
| Pencil hardness | HB | B | HB | HB | B | HB | HB |

What is claimed is:

1. A resinous composition comprising a compound or resin having a plurality of epoxy groups in the molecule, and a catalytically effective amount of a superacid salt of an N,N'-di- or N,N',N'-trisubstituted urea produced by reacting an organic isocyanate and a primary or secondary amine, at least one of said isocyanate and said amine being monofunctional.

2. The resinous composition as claimed in claim 1, wherein said superacid is $HSbF_6$, $HBF_4$, $HAsF_6$, $HPF_6$ or $HCF_3SO_3$.

3. The resinous composition as claimed in claim 1, wherein both of said isocyanate and said amine are monofunctional.

4. The resinous composition as claimed in claim 1, wherein one of said isocyanate and said amine is monofunctional and the other is polyfunctional.

5. The resinous composition as claimed in claim 1, wherein said epoxy groups are non-alicyclic epoxy groups.

6. The resinous composition as claimed in claim 5, wherein said non-alicyclic epoxy groups are glycidyl.

7. The resinous composition as claimed in claim 1, wherein said epoxy groups are alicyclic epoxy groups.

8. The resinous composition as claimed in claim 7, wherein said alicyclic epoxy groups are epoxycyclohexyl.

9. A method of curing at room temperature a curable resinous composition comprising a compound or resin having a plurality of epoxy groups in the molecule, which comprises mixing the resinous composition at ambient temperature with a catalytically effective amount of a superacid salt of an N,N'-di- or N,N',N'-trisubstituted urea produced by reacting an organic isocyanate and a primary or secondary amine, at least one of said isocyanate and said amine being monofunctional.

10. The method as claimed in claim 9, wherein said superacid is $HSbF_6$, $HBF_4$, $HAsF_6$, $HPF_6$ or $HCF_3SO_3$.

11. The method as claimed in claim 9, wherein both of said isocyanate and said amine are monofunctional.

12. The method as claimed in claim 9, wherein one of said isocyanate and said amine is monofunctional and the other is polyfunctional.

13. The method as claimed in claim 9, wherein said epoxy groups are non-alicyclic epoxy groups.

14. The method as claimed in claim 13, wherein said non-alicyclic epoxy groups are glycidyl.

15. The method as claimed in claim 9, wherein said epoxy groups are alicyclic epoxy groups.

16. The method as claimed in claim 15, wherein said alicyclic epoxy groups are epoxycyclohexyl.

* * * * *